(12) United States Patent
Nielsen (10) Patent No.: US 10,265,216 B2
(45) Date of Patent: Apr. 23, 2019

(54) DEVICE FOR APPLYING AN OPHTHALMIC FLUID

(71) Applicant: EYE-GO A/S, Espergærde (DK)

(72) Inventor: Søren Anker Nielsen, Espergærde (DK)

(73) Assignee: EYE-GO A/S, Espergaerde (DK)

( * ) Notice: Subject to any disclaimer, the term of this patent is extended or adjusted under 35 U.S.C. 154(b) by 280 days.

(21) Appl. No.: 15/115,462

(22) PCT Filed: Feb. 2, 2015

(86) PCT No.: PCT/EP2015/052072
§ 371 (c)(1),
(2) Date: Jul. 29, 2016

(87) PCT Pub. No.: WO2015/114139
PCT Pub. Date: Aug. 6, 2015

(65) Prior Publication Data
US 2017/0007449 A1    Jan. 12, 2017

(30) Foreign Application Priority Data

Jan. 31, 2014 (DK) ................................. 2014 70045
Jan. 31, 2014 (DK) ................................. 2014 70046

(51) Int. Cl.
*A61M 11/02* (2006.01)
*A61F 9/00* (2006.01)
(Continued)

(52) U.S. Cl.
CPC .......... *A61F 9/0026* (2013.01); *A61F 9/0008* (2013.01); *A61M 11/007* (2014.02);
(Continued)

(58) Field of Classification Search
CPC ... A61F 9/0008; A61F 9/0026; A61M 11/007; A61M 11/008; A61M 11/02;
(Continued)

(56) References Cited

U.S. PATENT DOCUMENTS 2,524,720 A * 10/1950 Watrous ................ A61F 9/0008
528/26
3,934,585 A    1/1976 Maurice
(Continued)

FOREIGN PATENT DOCUMENTS

EP         925799 A2    6/1999
EP        1262307 A2   12/2002
(Continued)

OTHER PUBLICATIONS

Patent Abstracts of Japan for JP 2005021254, dated Jan. 27, 2005, 1 page.
(Continued)

*Primary Examiner* — Susan S Su
(74) *Attorney, Agent, or Firm* — McDermott Will & Emery LLP (57) ABSTRACT

A device for dispensing a mist of an ophthalmic fluid includes a discharge opening for said mist, a mixing chamber communicating with said discharge opening, an air chamber holding a volume of air, a first drive operable to expel air from said air chamber, a fluid chamber for holding a volume of the fluid to be dispensed and communicating with said mixing chamber, a second drive for delivering a predetermined dose of said fluid to said fluid chamber, said air chamber communicating with said fluid chamber and with said mixing chamber, said device establishing one flow of expelled air flowing into said fluid chamber, so as to force liquid from said fluid chamber into said mixing chamber, and another flow of said expelled air flowing past said fluid chamber into said mixing chamber.

18 Claims, 5 Drawing Sheets

(51) Int. Cl.
*B05B 11/00* (2006.01)
*A61M 11/00* (2006.01)
*B05B 7/04* (2006.01)
*B05B 7/24* (2006.01)
*A61M 11/06* (2006.01)

(52) U.S. Cl.
CPC .......... *B05B 7/0475* (2013.01); *B05B 7/2443* (2013.01); *B05B 7/2464* (2013.01); *B05B 7/2491* (2013.01); *B05B 11/3087* (2013.01); *A61M 11/06* (2013.01); *A61M 2210/0612* (2013.01)

(58) Field of Classification Search
CPC .......... A61M 11/06; A61M 2210/0612; A61M 11/08; B05B 11/3087; B05B 7/0475; B05B 7/2443; B05B 7/2464; B05B 7/2491
USPC .................................. 604/296, 300
See application file for complete search history.

(56) References Cited

U.S. PATENT DOCUMENTS

| | | |
|---|---|---|
| 5,997,518 A | 12/1999 | Laibovitz et al. |
| 6,053,364 A | 4/2000 | van der Heijden |
| 6,159,188 A | 12/2000 | Laibovitz et al. |
| 6,213,982 B1 | 4/2001 | Py |
| 7,226,435 B2 | 6/2007 | Darnell |
| 7,314,187 B2 | 1/2008 | Hochrainer et al. |
| 7,621,897 B1 | 11/2009 | Berke |
| 7,883,031 B2 | 2/2011 | Collins, Jr. et al. |
| 8,012,136 B2 | 9/2011 | Collins, Jr. et al. |
| 8,545,463 B2 | 10/2013 | Collins, Jr. et al. |
| 8,684,980 B2 | 4/2014 | Hunter et al. |
| 8,936,021 B2 | 1/2015 | Collins, Jr. |
| RE45,589 E | 6/2015 | Py |
| 2002/0161344 A1 | 10/2002 | Peclat et al. |
| 2005/0240162 A1 | 10/2005 | Chen et al. |
| 2006/0011657 A1 | 1/2006 | Wright |
| 2008/0097359 A1 | 4/2008 | Hochrainer et al. |
| 2009/0043269 A1 | 2/2009 | Skou et al. |
| 2009/0247967 A1* | 10/2009 | Delli Paoli, Jr. . A61M 16/0666 604/300 |
| 2010/0222752 A1* | 9/2010 | Collins, Jr. .......... A61M 11/005 604/296 |
| 2010/0331765 A1 | 12/2010 | Sullivan |
| 2012/0272952 A1* | 11/2012 | Hsiao .................. A61M 11/005 128/200.16 |
| 2014/0213989 A1 | 7/2014 | Kelly |

FOREIGN PATENT DOCUMENTS

| | | |
|---|---|---|
| EP | 1624938 A1 | 2/2006 |
| EP | 2361075 A1 | 8/2011 |
| GB | 1321506 A | 6/1973 |
| JP | 2005-21254 | 1/2005 |
| WO | WO-97/13585 A1 | 4/1997 |
| WO | WO-02/062488 A1 | 8/2002 |
| WO | WO-2005/016219 A1 | 2/2005 |
| WO | WO-2006/044029 A2 | 4/2006 |
| WO | WO-2006/076922 A1 | 7/2006 |
| WO | WO-2007/132446 A2 | 11/2007 |
| WO | WO-2008/041177 A2 | 4/2008 |
| WO | WO-2010/018118 A1 | 2/2010 |
| WO | WO-2011/010310 A1 | 1/2011 |
| WO | WO-2012/009696 A2 | 1/2012 |
| WO | WO-2012/009702 A1 | 1/2012 |
| WO | WO-2012/009706 A1 | 1/2012 |
| WO | WO-2012/072551 A1 | 6/2012 |
| WO | WO-2012/101634 A2 | 8/2012 |
| WO | WO-2012/159026 A1 | 11/2012 |
| WO | WO-2013/090459 A1 | 6/2013 |
| WO | WO-2013/090468 A1 | 6/2013 |
| WO | WO-2013/155201 A2 | 10/2013 |
| WO | WO-2013/158967 A2 | 10/2013 |
| WO | WO-2013/169988 A1 | 11/2013 |
| WO | WO-2013/169990 A1 | 11/2013 |
| WO | WO-2013/173321 A1 | 11/2013 |
| WO | WO-2013/173495 A1 | 11/2013 |

OTHER PUBLICATIONS

English Translation of Notice of Reasons for Rejection for Japanese application No. 2016-567158, dated Nov. 26, 2018, 6 pages.

* cited by examiner

DEVICE FOR APPLYING AN OPHTHALMIC FLUID

CROSS-REFERENCE TO RELATED APPLICATIONS

This application is the U.S. National Phase under 35 U.S.C. § 371 of International Application No. PCT/EP2015/052072, filed on Feb. 2, 2015, which claims priority to Danish application Nos. PA201470045 and PA201470046, both filed on Jan. 31, 2014. The entire contents of these applications are incorporated by reference herein.

The present disclosure relates generally to a device for dispensing a mist of an ophthalmic liquid fluid.

Such devices are already known and vary in structure and design. By way of example devices are known that comprise a squeeze bottle squeezed by the user to expel the liquid fluid as a mist.

Below prior art references disclose different designs of such devices.

U.S. Pat. No. 5,997,518 A teach a device and method for delivering small microliter volumes of liquid preparations to the eye or other body part. The device and method propose to apply a gas stream to induce a controlled, preselected volume of liquid into the gas stream and to deliver the liquid in the form of small droplets to the desired site.

The present disclosure departs from U.S. Pat. No. 5,997,518 A inter alia in that the device according to the present disclosure includes a second drive, or a dosage drive/pump, for delivering liquid fluid to a user's eye.

U.S. Pat. No. 3,934,585 A teach a method and apparatus for applying therapeutic eye drops to the eye by metering a predetermined volume of fluid and rapidly applying a pressure to one end of the metered fluid for forcing the fluid from a nozzle.

US 2009/043269 A teach a liquid dispensing apparatus including a liquid storage space. The device includes a nozzle for dispensing liquid. Fluid is expelled through the nozzle by a movable wall operable to reduce the liquid storage space. The apparatus also includes an intermediate storage space having variable volume; the intermediate storage space including a liquid inlet in fluid communication with the liquid storage space for receiving liquid therefrom. A specific amount of the liquid is transferred from the liquid storage space to the intermediate storage space in a single operation.

US 2002/161344 A teach a device and use method for ejecting a liquid stream towards an eye. The device includes a pump mechanism operable to deliver at least part of the liquid from a container through the opening to form a stream of liquid. The pump mechanism may include a pump driver able to store cocked energy for driving the pump mechanism and at least one activation mechanism may be present and operable to initiate the device for the liquid delivery, whereby a driving mechanism is arranged to transform manual or stored energy into cocked energy.

US 2014/213989 A teach a fluid dispenser suitable for ophthalmic treatments and delivering of ophthalmic agents such as eye drops. The fluid dispenser incorporates a tube made from compliant materials as the key dosing component. A first point and a second point on the tube may be acted upon by folding the tube or by external elements, making the segment between the first point and the second point a squeezing section that houses a dosing chamber.

The squeezing section may be pressed by an anvil or other structures, pressurizing the fluid contained in the dosing chamber so that once the tube is released on one point, the fluid in the dosing chamber is discharged. With each dosing process, a single dose of the fluid is discharged. In addition, the fluid dispenser is capable of delivering a series of doses of the fluid by repeating the dosing process.

Generally, however, the liquid fluid exits the bottle as rather larger droplets and it is difficult if not impossible for the user to dispense an exact dose of the liquid fluid, which may be required where the user is under treatment for an ophthalmic disease or condition, such as dry eyes.

The present disclosure seeks to overcome such problems with the prior art dispensers, without compromising the need to provide a simple and user friendly dispenser which allows for repeated discharge of a dose of a medical ophthalmic fluid.

Broadly speaking the inventor has identified two fundamental aspects, as indicated in the appended claims and which may be combined.

According to one aspect fine, or relatively fine, droplets are achieved even where a liquid fluid of medium viscosity, such as in the order of 1-100 mPa.s is dispensed, through the action of a dedicated air flow, while according to another aspect a repeated discharge of identical doses is made possible. At the same time, through the disclosure it becomes possible to dispense the ophthalmic liquid fluid irrespectively of the user holding his head upright or tilted, or even if the user is in bed lying down.

Specifically, according to the first aspect as defined broadly in claim 1—the device comprises a discharge opening, possibly formed by a spray nozzle, for discharging a mist of fluid, a mixing chamber communicating with the discharge opening, an air chamber for holding a volume of air, a first drive operable to expel air from the air chamber, a fluid chamber for holding a volume of the fluid to be dispensed and communicating with the mixing chamber, a second drive for delivering a predetermined dose of the fluid to the fluid chamber and configured for communicating with a supply of the fluid, such as a container, the air chamber communicating with the fluid chamber and separately with the mixing chamber, and the device being configured for establishing one flow of the expelled air flowing into the fluid chamber, so as to drive the said volume of liquid from the fluid chamber into the mixing chamber, and another flow of the said expelled air flowing past the fluid chamber into the mixing chamber, for assisted atomizing of the fluid by the said other flow of air striking the fluid driven into the mixing chamber. This allows for the user to obtain a very fine mist of the fluid required where the fluid has a high viscosity and concentration, as may be the case in certain applications and for treating certain ophthalmic diseases or conditions, such as dry eyes, requiring the deposition of low to high viscosity fluid on a person's cornea.

To provide a high certainty that a uniform dose of the fluid is applied each time the device may include a peristaltic pump or similar in fluid connection with the aforementioned fluid chamber. It is also contemplated to include a mechanism allowing for a user to bring the device into a configuration ready for dispensing using a minimum of manual force, which may be required where to device is to be used by eg. an elderly person. For that purpose the device may further comprise a rotatable head or handle, a piston including a rod and a piston head received in a structure, such as a cylinder, defining the air chamber, the rod and the handle including a winding track and a stationary tab slidably received therein therewith, for displacing by rotation of the handle the piston to a retracted position for holding the volume of air in the air chamber, and a lock and release mechanism for locking and releasing the piston in and from 
the retracted position, for a spring forming the aforementioned first drive to drive the piston towards an advanced position, giving rise to said expelling.

According to another aspect, a high certainty that a uniform dose of the fluid is applied each time is achievable even where the liquid fluid does not require any fluid/air mixing by supply of a separate air flow as discussed above, by incorporating a peristaltic pump or equivalent positive displacement pump in a device for dispensing. The device having the following characteristics: a spray nozzle for generating a mist of a fluid, an air chamber for holding a volume of air, a first drive operable to expel air from the air chamber, a liquid fluid chamber for holding a volume of the liquid fluid to be dispensed and communicating with the nozzle, a second drive comprising the peristaltic pump and in fluid communication with the fluid chamber, for delivering a predetermined dose of the liquid fluid to the liquid fluid chamber, the peristaltic pump being configured for communicating with a supply of the fluid, such as a container, the air chamber being in fluid communication with the liquid fluid chamber, and by the device being configured for establishing a flow of the said expelled air flowing into the fluid chamber to force the said volume of fluid, or essentially all said volume of fluid therein, from the fluid chamber towards the nozzle.

Embodiments of the disclosure are defined in the dependent claims, the objects of which will appear from the following.

A presently preferred embodiment of the disclosure will now be described with reference to the appended drawings; the following description is not intended to limit the scope of the present disclosure which is defined by the claims.

FIG. 1 is a side view of an embodiment of the device of the disclosure,

FIG. 2 is a perspective view of a component structure of the device,

FIG. 3 is a perspective view of the device, with an end cap and shown with the device casing partially cut away, FIG. 4 is a cross-sectional view of the device in a configuration prepared for dispensing a mist of fluid, and FIG. 5 is another cross-sectional view of the device, perpendicular to that of FIG. 4 and in a configuration after dispensing of a mist of fluid.

FIG. 1 shows an embodiment of a device 1 according to the present disclosure, for repeated dispensing of a mist of an ophthalmic liquid fluid into a person's eye/onto a person's cornea (not shown); the device of the disclosure is particularly but not exclusively useful for dispensing a mist of such a fluid having a relatively high viscosity and is preferably sized to allow an average person to hold it in his/her hand.

The shown device 1 comprises an eyelid opener portion 10 and a casing portion 20. The eyelid opener portion 10 is configured for keeping a person's eyelid open by being held against the eye region during the dispensing and includes a collar 12 and a connecting structure 14 connecting the collar 12 with a front end F of the casing 20. A discharge opening or nozzle 25, which may by way of example be circular or oval, for dispensing the aforementioned mist in the direction towards the collar 12 and, hence, the eye (not shown), is located at the front end F.

The device 1 generally includes various mechanisms or drives located inside the casing 20 and operable by a person through various operating parts which may include, as shown, one or more of following: a rotatable handle 26, a depressible tab 30, and a rotatable head 28 defining the rear end R of the casing 20.

Two or more of the shown operating parts 26, 28, 30 may in other embodiments be combined into a single operating part such that more than one of the aforementioned mechanisms or drives are operable by the user manipulating only one operating part.

FIG. 2 shows an internal component structure generally designated numeral 50 and mounted inside the casing 20. The component structure 50 supports at one end an outlet structure including the discharge opening 25 and at the other end the rotatable device head 28. The rotatable head 28 has a tubular extension 28' and is configured to snap into engagement with the casing 20 via flexible tabs 29, for assisting in the assembly of the device 1.

The component structure 50 comprises inter alia a container or barrel 70 containing the ophthalmic liquid fluid to be dispensed as a mist, and a first drive for user controlled advancing of a piston 55 with a piston rod and a head (the head not being visible in FIG. 2) received by a piston cylinder 60.

The cylinder 60 is configured for storing a first volume of air in an internal air chamber when the piston 55 is in a first, normally fully retracted position. The barrel 70 preferably has a movable bottom 72 and/or may be collapsible, has an internal volume allowing for dispensing of multiple doses of the ophthalmic fluid, and may be replaceable to allow for replacement with another and, hence, continued use of the device 1 after one barrel 70 has been emptied.

For the reason explained below the rod of the piston 55 is preferably held against rotation about its longitudinal axis and is generally movable to its first, retracted position from a second, advanced position shown in FIG. 2 by rotation of the rotatable device head 28 about an axis parallel with the longitudinal axis of the rod of the piston 55.

A proximal end part of the rod of the piston 55 remote from the head is shown in FIG. 2 and is configured to be receivable within the tubular extension 28' of the rotatable device head 28. The rod of the piston 55 has surface track 56 including a spirally winding portion as well as a straight portion 56'. The winding portion of the surface track 56 slidably receives a tab located on the inside of the tubular extension 28' whereby rotation of the rotatable head 28 relative to the piston rod brings about a corresponding displacement of the piston 55 from the second position to the retracted first position in which a length of the proximal end part of the rod of the piston 55 shown in FIG. 2 is received within the tubular extension 28' of the rotatable head 28.

The component structure 50 also may include a second drive, preferably in the form of a peristaltic dosing pump 82 or similar, for dispensing a required dose of the liquid fluid into a liquid chamber and/or a mixing chamber to be discussed further below and located at the fore end of the cylinder 60, inside thereof and closest to the discharge opening 25. Shown in FIG. 2 is also a tube 80, preferably a tube flexible along its entire length, which has a first portion 81 and a second portion 81' and which is used for drawing the liquid fluid from the barrel 70. The tube 80 connects the barrel 70 with the aforementioned mixing chamber at a connection point 81", via the second drive, eg. the peristaltic dosing pump 82 discussed further below.

The peristaltic pump 82 includes a housing with a peripheral wall portion 87, shown as a semi-circular wall portion 87, as well as a rotatable disc 84 carrying on the one hand a handle 26 for manually operating the pump 82 and on the other hand two radially oppositely lodged shoes or rollers, of which one roller 86 is seen best in FIG. 2 while the opposite roller 86' is seen in FIG. 3. A flexible portion of the tube 80 is received between the wall portion 87 and the rotatable disc 84 and is locally squeezed flat between the wall portion 87 and each of the two rollers 86. The length of the tube 80 between the locally flattened parts thereof defines a volume or dose of the fluid inside that length which is driven forward into the second portion 81' of the tube 80 by the user rotating the disc 84 and, hence, moving the rollers 86, 86' along the wall portion 87 and the tube portion between disc 84 and the wall portion 87. A mechanism (not shown) may be included for limiting rotation of the rotatable disc 84 by eg. 180° per operation, such that manipulation of the handle 26 only allows the user to draw a single dose of predetermined volume of the liquid fluid from the barrel 70 until the time that mechanism is released. It will be understood that proper configuration of the tube 80 and the container 70 ensures that a corresponding volume of the liquid fluid in the container 70 is drawn from the container 70 as the dose is driven forward into the second portion 81' of the tube 80 in the manner described above. By using a collapsible container or reservoir 70, or a container 70 with a displaceable bottom, suction applied by the peristaltic pump 82 makes it possible to ensure a complete emptying of the container 70.

Other forms of dosing pumps, or positive displacement pumps, may be applied and/or incorporated without departing from the present disclosure.

The second drive may be provided with, integrally or not, not shown valve means configured for hindering flow of liquid fluid when the second drive is passive. In embodiments wherein the second drive includes a piston pump, said not shown valve means may be actuated by the piston resting in an extended, i.e. not retracted, position.

The device 1 may be configured such that the first and the second drives may be activated and/or retracted by means of one button or handle only; eg. the device head 28 and the handle 26. Furthermore, the device 1 may be configured such that first and/or the second drives may be activated and/or retracted and/or released by means of applying a linear force to a pushbutton.

The container 70 may, in one embodiment, constitute a collapsible bag or pouch made eg. from thin and/or flexible foil; possibly closed by welding. Alternatively, the container 70 may constitute a moulded plastic component.

The container 70 may, in one embodiment, constitute a cylinder including a movable piston. The movable piston may define the bottom of the cylinder and the distal fixed end may be provided with means for hydraulic and/or mechanical interface to the device 1. Means, such as a spring, may be provided in order to urge or push the piston into the cylinder. By this, liquid dosing may be facilitated.

The container 70 may, in one embodiment, be joined to a preferably moulded plastic component allowing for hydraulic and/or mechanical interface to the device 1.

The liquid container 70 may be integrated with the wet part of the device 1, preferably in a manner allowing for exchangeability of the container 70.

The separate container 70 may have a unique shape for mechanical orientation and/or fixation of the container with respect to the device 1.

Figure 3:
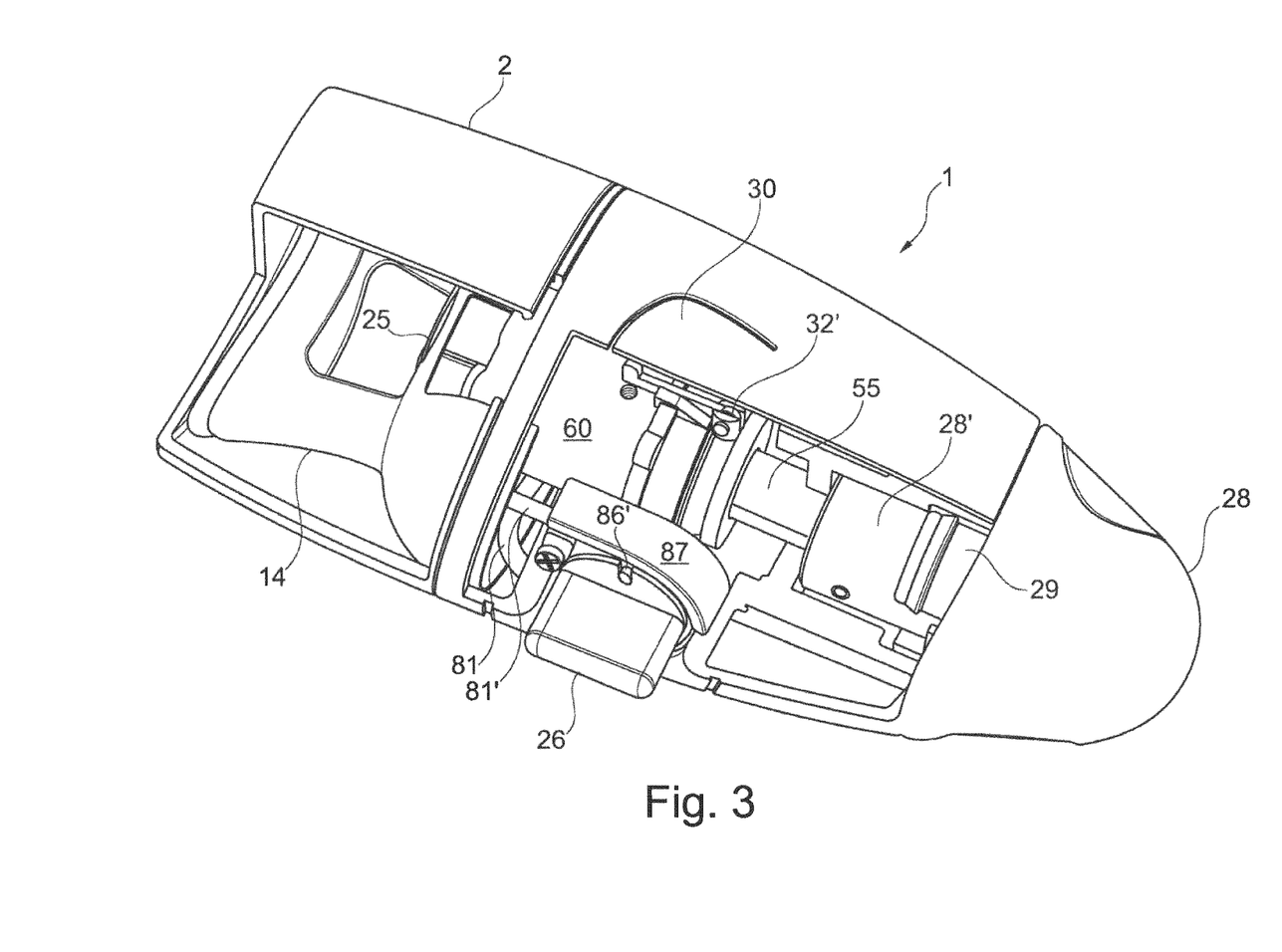

FIG. 3 shows the device 1 with a protective cap 2 mounted onto the front end F.

As can be seen the device 1 of the shown embodiment has a relatively flat casing 20, such as one with a length and width in the order of about 90 mm and 60 mm, respectively, allowing it to be conveniently held by the user.

Figure 1:
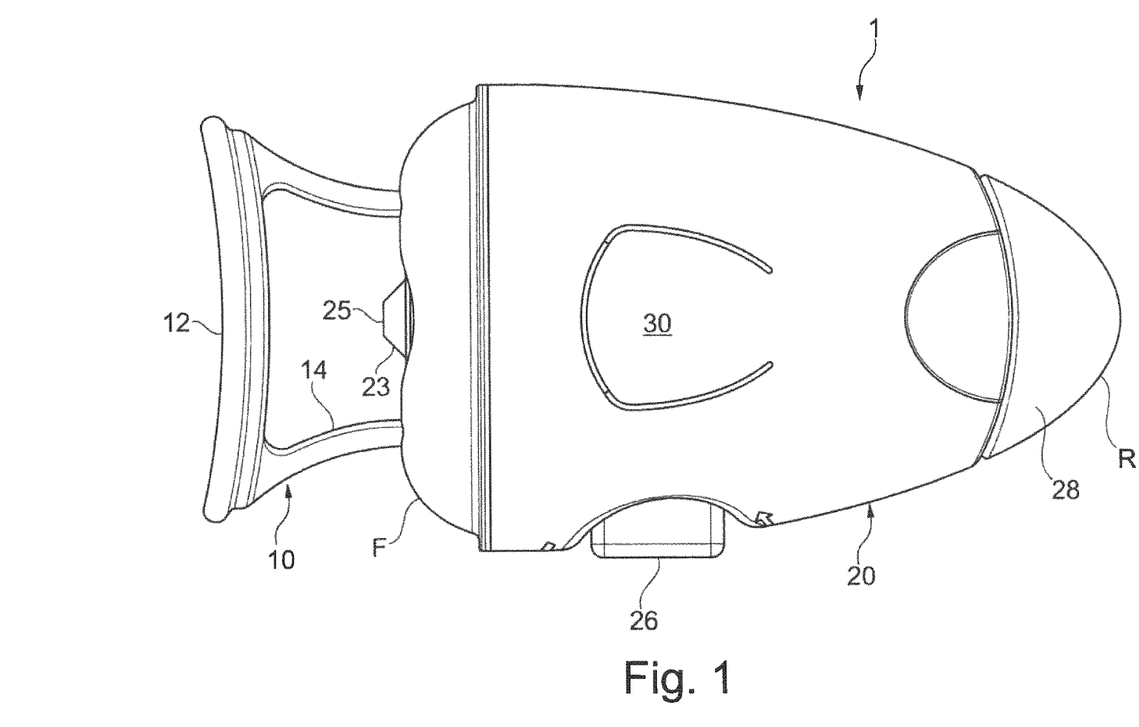
Figure 2:
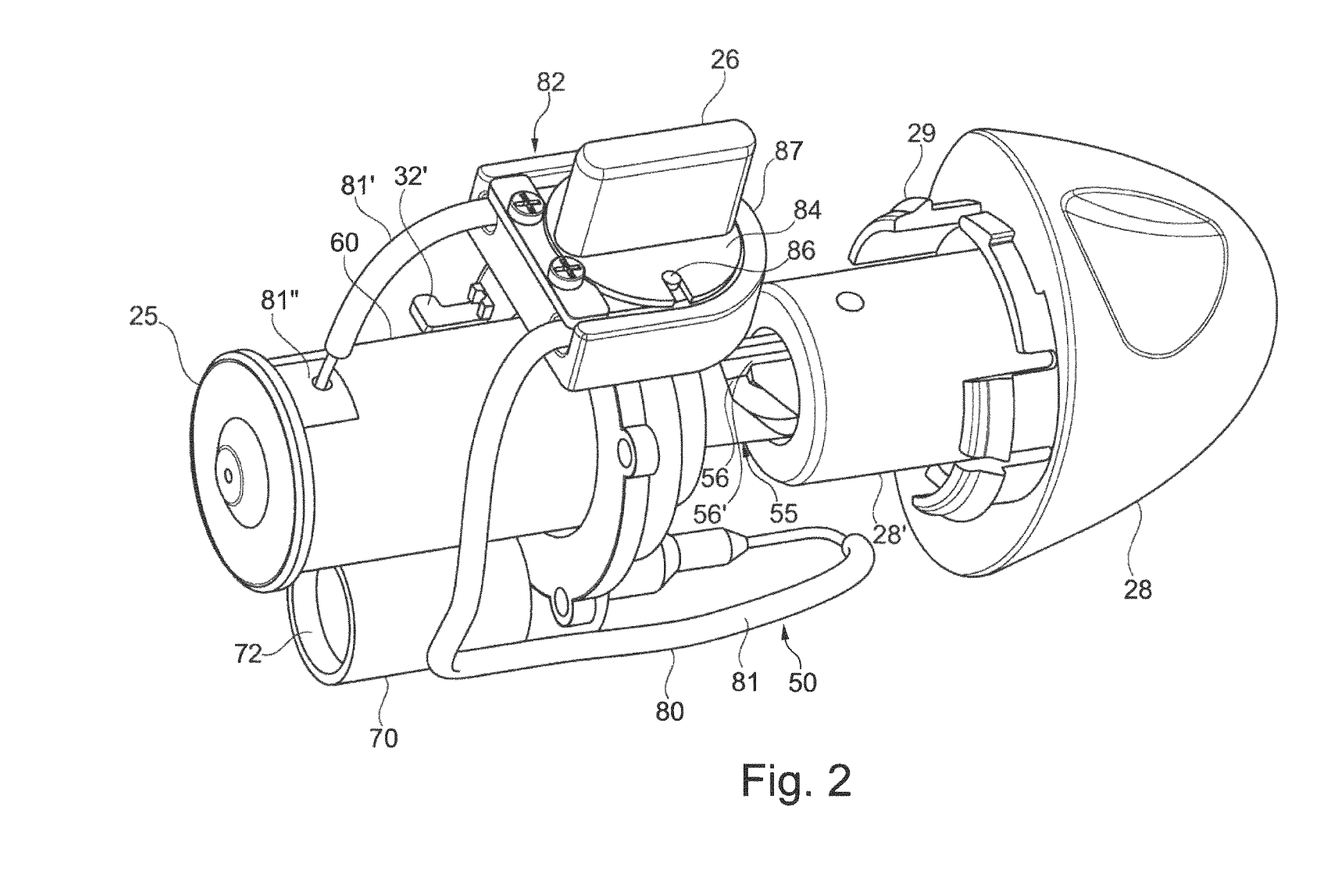
Figure 4:
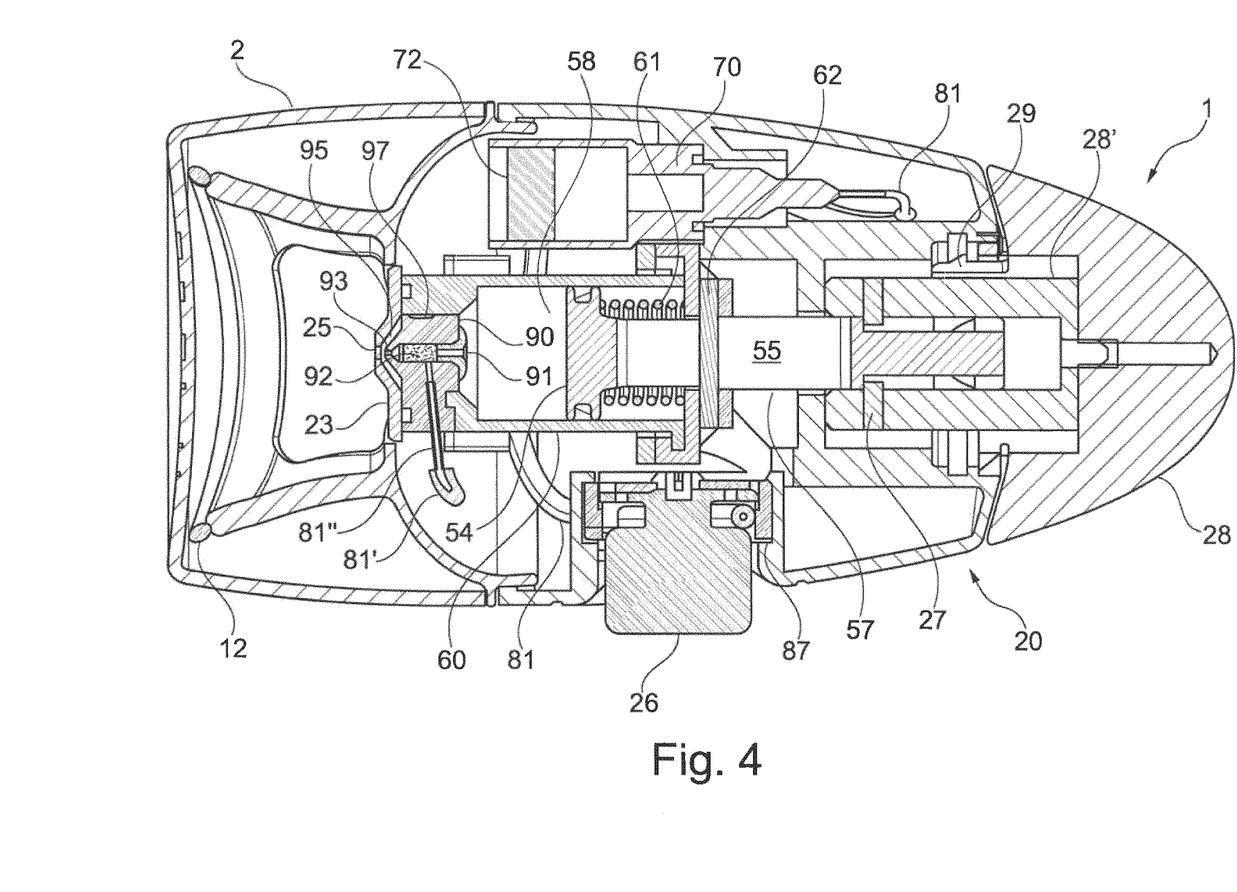
Figure 5:
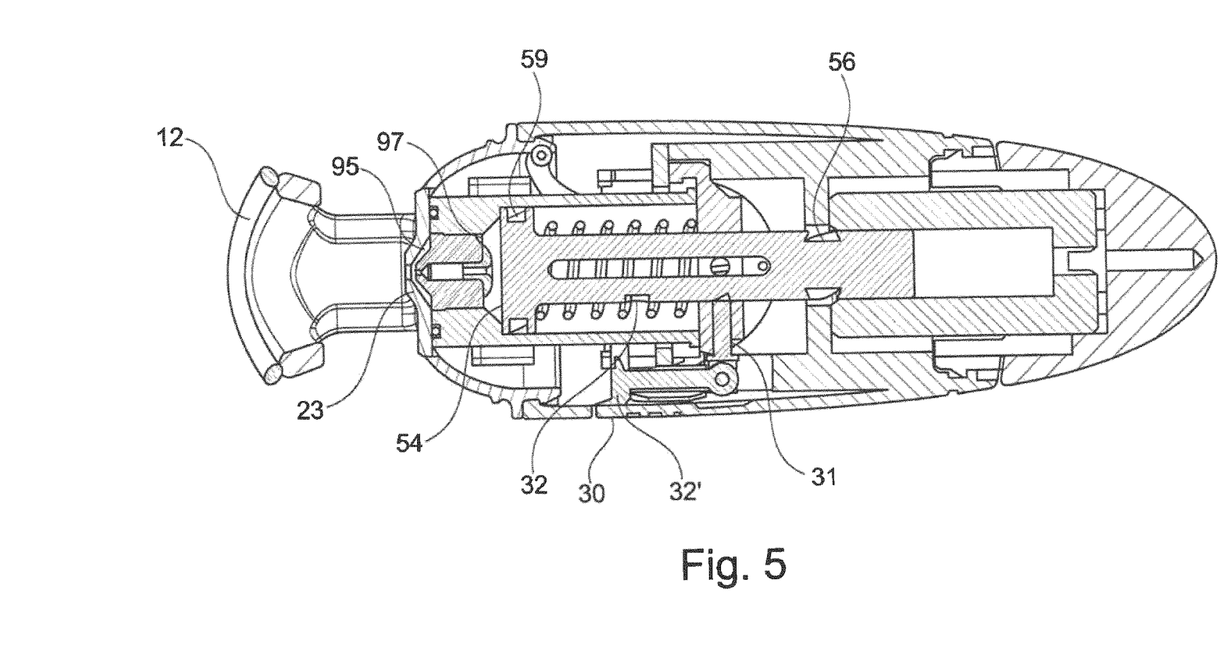

Turning to FIGS. 4 and 5 details of a presently preferred embodiment of the disclosure is shown in FIGS. 1-3 and will now be discussed.

FIG. 4 shows the device 1 in the first, retracted position of the piston 55, i.e. where the head 54 of the piston is positioned distant from the discharge opening 25 and where a relatively large length of the proximal end part of the rod 57 of the piston 55 is received within the tubular extension 28' of the rotatable head 28. The user may displace the piston 55 relative to the cylinder 60 to this first position by rotating the head 28; this displacement is against the force of a spring 61 configured to bias the piston 55 towards the aforementioned second, advanced position by being compressed between the piston head 54 and a rear closure 62 of the cylinder 60. The aforementioned tab located inside the tubular extension 28' and engaging the spirally winding portion of surface track 56 is shown in FIG. 4 by numeral 27, and by selecting an appropriate design of the spirally winding portion of the surface track 56 a desired displacement of the piston 55 is achieved by rotating the head 28 through eg. 180° to 360°, thus allowing also users with reduced manual strength to retract the piston 55 against the force of the spring 61, with a relatively small effort.

In the first position of the piston 55 shown in FIG. 4 the tab 27 is aligned with the straight portion 56' of the surface track 56, the piston 55 being ready for moving axially along the length of the extension 28' to its second position, driven by the spring 61 upon the user releasing a lock mechanism. The lock mechanism comprises a locking rib 31 connected to the depressible tab 30 (see FIG. 1) and engaging a recess 32 formed in the outer face of the cylinder 60. The rib 31 and the recess 32 are best seen in FIG. 5. The depressible tab 30 acts as a lever mechanism by including a depressible arm 32' also shown in FIG. 2, whereby depression of the tab 30 draws the locking rib 31 located at the other end of arm 32' out of engagement with the recess 32 such that the piston 55 is released to move forward to its advanced second position, driven by the spring 61.

As shown in FIG. 4, in the first position of the piston 55 an air chamber 58 in the cylinder 60 has a volume of air of, by way of example, about 820 mm$^3$, between the head 54 of the piston 55 and a dispensing structure generally indicated by numeral 90.

As the piston 55 is displaced by the user towards the retracted first position, in the depicted embodiment by rotation of the rotatable head 28, air is simultaneously drawn into this air chamber 58 through an air access port. The discharge opening 25 for discharging the mist may be used for this purpose; however, to reduce the risk of contamination of the air chamber 58 by already dispensed liquid fluid being drawn back in together with fresh air the air access port is preferably located elsewhere, such as in the peripheral wall of the cylinder 60 and is preferably equipped with a one-way valve (not shown). Another not shown one-way valve may be located in connection with the discharge opening 25 to prevent or restrict air entry, to prevent the aforementioned contamination. In this manner there is a reduced need for using liquid fluids with preservatives.

The dispensing structure 90 is preferably inserted into the cylinder 60 to define the foremost end thereof, opposite the rear closure 62. As shown, a passage 91 for a first air flow leads from the air chamber 58 into an internal liquid chamber 92 within the structure 90. One or more secondary passages 97, such as three, preferably winding (eg. spirally) around the dispensing structure 90 as in the shown embodiment, are formed and arranged to communicate with the air chamber 58 on the one hand and with a mixing chamber 95 on the other hand. The mixing chamber 95 is located in front of the dispensing structure 90 and defined between the dispensing structure 90 and a front casing part 23 that has an aperture defining the discharge opening 25. The one or more secondary passages 97, which may have circular cross-section(s), allow for a second air flow to flow past the structure 90 and, hence, the liquid chamber 92, i.e. not through the liquid chamber 92, to enter the mixing chamber 95.

The dispensing structure 90 may be provided with a laterally oriented port or passage to allow for a liquid flow to the internal liquid fluid chamber 92 from the second portion 81' of the tube 80 via connection point 81", and also has a discharge opening 93 opposite the passage 91. The mixing chamber 95 may, as shown in FIGS. 4 and 5, follow the general contour of a saucer, with opening 25 being opposite and aligned with the more narrow opening 93 and with the secondary passages 97 opening into the mixing chamber 95 at the "rim" of the saucer. Valves (not shown) opening at a certain pressure may be provided at the normally narrow discharge opening 93 and in passage 91 to retain liquid fluid in the liquid fluid chamber 92, but may be dispensed with, in particular where the liquid fluid has a relatively high viscosity.

The volume of the liquid fluid chamber 92 corresponds to the aforementioned volume of the dose of liquid fluid dispensed or dosed by the peristaltic pump 82 upon correct manipulation thereof, i.e. proper rotation of the disc 84 through a given angle, by means of handle 26, and may by way of example be in the order of about 50 mm$^3$. The passage 91, opening 93 and fluid chamber 92 may have a circular cross-section.

When preparing the device 1 for use after a previous discharge/dispensing or when taking the device 1 into use for the first time, a person will fill the fluid chamber 92 using the second drive, in the shown embodiment the peristaltic pump 82, and also withdraw the piston 55 to the retracted, first position. This may, in principle, occur in any sequence, or simultaneously if a single operating part is used for the peristaltic pump 82 and the piston 55. In FIG. 4 the fluid in fluid chamber 92 is represented by dots.

On subsequent release of the first drive, in the shown embodiment constituted by the spring 61 which advances the piston 55, air in the air chamber 58 drawn into the cylinder 60 during the preceding withdrawal of the piston 55 is forced out of the cylinder 60 into the liquid fluid chamber 92 within the structure 90 through the passage 91, and preferably also leaves the cylinder 60 as the aforementioned second air flow through the series of additional passages 97 opening up into the mixing chamber 95. The terms "first" and "second" used in this respect are not intended to imply any necessary time wise delay between the two flows of air but primarily to reflect that several flows of air are generated, normally having different purposes, the first air flow primarily serving to force liquid fluid out of the liquid fluid chamber 92. After all liquid fluid has been forced/driven out of liquid fluid chamber 92 any remaining air in the air chamber 58 may still be discharged into the mixing chamber 95 through the liquid fluid chamber 92.

It will be understood that the speed of the second flow of air leaving the air chamber 58 is preferably high and that the first flow of air discharged by the action of the spring 61 ejects or pushes the liquid fluid out from the liquid fluid chamber 92 through the discharge opening 93 at the forward end of the liquid fluid chamber 92, into the mixing chamber 95. Flow of the liquid fluid into the mixing chamber 95 may be assisted by any venturi effect arising from the inflow into the mixing chamber 95 of the secondary air flow. A fine mist of the liquid fluid is generated, even where the fluid has a medium to high viscosity, by the second air flow leaving the secondary passages 97 impinging on the simultaneously ejected liquid fluid, in front of the discharge opening 93.

It is contemplated to design the course of the one or more passages 97 such that the forward second air flow preferably strikes the ejected liquid fluid at an acute angle with respect to the general forward direction of flow of the ejected liquid fluid. The fine mist generated thereby exits the device 1 through the discharge opening 25 with high inertia, as determined i.a. by the spring 61, towards the eye of the user, which eye is held open by the eyelid opener portion 10. By properly adjusting the volume of air in the air chamber 58 it may be ensured that all dispensed fluid is blown away from the device 1 during each dispensing.

By selecting the relative dimensions of the one or more passages 97 in relation to the dimension of passage 91 leading into the liquid fluid chamber 92 and the discharge opening 93 leading out there from any desired flow and droplet size may be obtained. It may in some instances be preferred that the liquid fluid is ejected into a second flow of air already prevailing in the mixing chamber 95.

The design of the discharge opening 25, normally located about 20-30 mm from the eye when the device 1 is correctly held, ensures that the mist is deposited only on the eye, and this may be achieved with the device 1 held in any orientation, horizontally or vertically.

As noted, in the shown embodiment the volume of the liquid fluid standing in the second tube portion 81' will remain therein during discharge of the liquid fluid in the liquid fluid chamber 92. The seal provided by the roller 86' of the peristaltic pump 82 prevents this volume from being drawn into the liquid fluid chamber 92 as the liquid fluid therein is ejected by the air.

All components of the device mentioned above may be of any desired material, such as a plastics material, a metal material or combinations thereof. Notably, the collar for keeping the user's eyelid open may carry a surface material with antibacterial properties or be formed from such a material. Furthermore, the components and/or surfaces defining and/or surrounding the discharge opening 25 and/or nozzle may be made from a material with antibacterial properties.

While it may be preferred to configure the device according to the disclosure such that first and second flows of air are established, which may be preferred where the liquid fluid has a high viscosity, in other cases it may not be required to provide for a secondary flow of air, by configuring the discharge opening 25 as a nozzle suitable for establishing by its geometry alone a small droplet size of the liquid fluid dispensed by the first drive.

The invention claimed is:

1. A device for dispensing a mist of an ophthalmic liquid fluid, comprising:
   a discharge opening for said mist,
   a mixing chamber communicating with said discharge opening,
   an air chamber for holding a volume of air,
   a first drive operable to expel air from said air chamber,
   a fluid chamber for holding a volume of the fluid to be dispensed and communicating with said mixing chamber,
   characterized in
   a second drive for delivering a predetermined dose of said fluid to said fluid chamber and communicating with or being configured for communicating with a supply of said fluid,
   said air chamber communicating with said fluid chamber and separately with said mixing chamber, 
said device being configured for establishing one flow of said expelled air flowing into said fluid chamber, so as to force said fluid from said fluid chamber into said mixing chamber, and another flow of said expelled air flowing past said fluid chamber into said mixing chamber, for assisted atomizing of said fluid by said other flow of air striking said fluid forced into said mixing chamber.

2. The device according to claim 1, including a container for said fluid.

3. The device according to claim 2, wherein said container is collapsible.

4. The device of claim 1, wherein said first drive comprising a spring, said spring acting on a displaceable piston in a structure, such as a cylinder, having said air chamber.

5. The device according to claim 4, further comprising:

a rotatable handle, said piston including a rod and a piston head received in said structure, said rod and said handle respectively including a winding track and a stationary tab slidably connected therewith, for displacing by rotation of said handle said piston to a retracted position for holding said volume of air in said air chamber, and a lock and release mechanism for locking and releasing said piston in and from said retracted position, for said spring to drive said piston towards an advanced position and providing for said expelling.

6. The device according to claim 1, said second drive comprising a liquid dosing pump configured for dose metering and for transferring fluid to said fluid chamber.

7. The device according to claim 6, wherein said liquid dosing pump is a piston pump.

8. The device according to claim 6, said liquid dosing pump being a positive displacement pump.

9. The device according to claim 1, said second drive comprising a peristaltic pump.

10. The device according to claim 9, wherein a flexible tube connects said peristaltic pump with a container containing said fluid.

11. The device according to claim 1, including an eyelid opener structure with a collar for keeping a person's eyelid open by being held against an eye region.

12. The device according to claim 1, wherein said device further includes:

a piston cylinder with said air chamber, a dispensing structure with a passage for said one air flow being at or defining the foremost end of said piston cylinder, a passage connecting said fluid chamber with said mixing chamber, said communication between said air chamber and said fluid chamber being by said passage for said one flow, and said separate communication between said air chamber and said mixing chamber being by one or more separate passages for said other flow.

13. The device according to claim 12, said dispensing structure including a laterally oriented port or passage for flow of said liquid fluid to said liquid fluid chamber.

14. The device according to claim 12, said one or more separate passages winding around said fluid chamber.

15. The device according to claim 1, wherein said first drive and/or said second drive is energized from a pressurized container or canister.

16. The device according to claim 1, wherein said first and said second drives are activated and/or retracted by means of one button or handle only.

17. The device according to claim 1, wherein said fluid chamber is in direct communication with said mixing chamber.

18. The device according to claim 1, wherein said fluid chamber is configured to accommodate a volume of liquid corresponding to one dose of liquid fluid.

* * * * *